United States Patent [19]

Malin et al.

[11] Patent Number: 5,108,176
[45] Date of Patent: Apr. 28, 1992

[54] METHOD OF CALIBRATING SCANNERS AND ARRANGEMENT FOR PRODUCING DEFINED SCATTERED LIGHT AMPLITUDES

[75] Inventors: Cosmas Malin, Mauren; Philip Hoyle, Vaduz, both of Liechtenstein

[73] Assignee: Censor AG, Vaduz, Liechtenstein

[21] Appl. No.: 527,051

[22] Filed: May 21, 1990

[30] Foreign Application Priority Data

Mar. 5, 1990 [CH] Switzerland .................. 00685/90

[51] Int. Cl.⁵ .............................................. G01N 21/88
[52] U.S. Cl. .................................. 356/237; 356/243
[58] Field of Search ............... 356/237, 243, 426, 342, 356/336; 250/252.1 A, 572

[56] References Cited

U.S. PATENT DOCUMENTS 4,776,693  10/1988  Imamura et al. ................... 356/237
4,966,457  10/1990  Hayano et al. ..................... 356/237

*Primary Examiner*—Vincent P. McGraw

[57] ABSTRACT

Calibration of a light scanner, particularly for measuring particles and surface finishes in the inspection of substrates uses a strongly scattering reference medium. A focused laser beam is directed onto the reference medium which is disposed outside the focal plane of the beam. Scattered light from the medium is thus defocused with respect to a photodetector that collects the scattered light. An amplifier connected to the photodetector measures the intensity of the scattered light. By the use of filters in the path of the light calibration of the optico-electronic system of the scanner is achieved.

9 Claims, 10 Drawing Sheets

METHOD OF CALIBRATING SCANNERS AND ARRANGEMENT FOR PRODUCING DEFINED SCATTERED LIGHT AMPLITUDES

BACKGROUND OF THE INVENTION

The present invention relates to a method of calibrating scanners and an arrangement for producing defined scattered light amplitudes, particularly for measuring particles and surface finishes during the inspection of substrates, for example wafers.

Devices which are based on the measurement of the elastic scattered light are used, inter alia, for the measurement of particles in air or on surfaces or for the inspection of surfaces (U.S. Pat. No. 4,314,763).

In such devices, the area to be observed is illuminated by a light source of high intensity and the scattered light is supplied to a photosensor—for example via a dark-field optical system. The photosensor (photodiode, photomultiplier) generates an electrical signal which is proportional to the amplitude of the scattered light and is fed to a following amplifier. On the assumption that the scattering capacity of a defect is related to its size, conclusions about the extent of the defect can be drawn from the scattered light amplitude.

This method of measuring has the disadvantage, however, that fluctuations in intensity of the light source, variations in the optical system (for example dark-field optical system or light source adjustment) and electronic drift in the photodetector or in the amplifier influence the result of the measurement at the output of the amplifier.

For this reason, attempts are made to compensate for such variations by means of various correction methods.

One such correction method consists in the regular measurement of the intensity of the light source. Fluctuations in the intensity can then be compensated for, as by varying the sensitivity of the photodetector or the amplifier. This method of correction has the disadvantage, however, that variations in the optical system, in the photodetector or in the amplifier, are not detected and are not taken into consideration.

Methods which include the whole of the light source, optical system, photodetector and amplifier for the calibration and measuring respectively are therefore better suited as correction methods.

Such methods used for this purpose a medium of known scattering capacity (reference medium) (as described for example in U.S. Pat. No. 4,512,659). Usually, in this case, the sensitivity of the photodetector and of the amplifier is altered with respect to the known medium until the desired value appears at the output of the amplifier. Thus with such a method, the accuracy of the calibration depends exclusively on the scattering capacity of the reference medium.

If very sensitive scattered-light devices are to be calibrated by this measuring method, however, the requirements regarding the reference medium have to be set particularly high, since a reference medium which produces very low scattered light amplitudes is extremely susceptible to variations (see in particular as described in U.S. Pat. No. 4,512,659).

If the reference medium is, for example, a surface with a very low scattering capacity, particles, air humidity, oxidation etc alter its scattering capacity drastically. In addition, the cleaning of such sensitive surfaces is extremely expensive and has to be carried out step-by-step in special cleaning processes. Contamination by particles has a particularly disadvantageous effect if the illuminated field is small. In this case, a single particle can alter the scattering capacity of the surface by some orders of magnitude.

Finally, the ability to produce surfaces thus prepared with an appropriately small scattering capacity limits the possible use of this method.

SUMMARY OF THE INVENTION

It is an object of the present invention to provide an arrangement for calibrating a scanner which is capable of producing particularly small, adjustable and defined scattered light amplitudes without being susceptible to contamination.

In a method and apparatus according to the invention an electro-optical system comprising a light source with a confocal optical system, a photodetector for the scattered light from the optical system and an amplifier for the photodetector output are calibrated by means of a reference medium with a known scattering capacity. The medium is strongly scattering and the scattered light amplitude is reduced by defocusing the reference medium. The local dependence of the scattered light amplitude is cancelled and an optical filter is superimposed in the optical system.

Such an arrangement covers all possible sources of drift. This has the very important advantage that it can be adapted to work with very low scattered light amplitudes. The arrangement is therefore largely insensitive to contamination with regard to sensitivity, accuracy and reliability, and can be cleaned easily. In addition, the desired scattered light values can be adjusted simply over a very wide range.

Two embodiments of the invention are described in more detail below with reference to the drawings.

BRIEF DESCRIPTION OF THE DRAWINGS

FIG. 1 shows a substrate surface inspection device, such as is used mainly for the inspection of wafers, in which apparatus according to the present invention can be employed. Apart from the smallest particles, it is also possible to reveal crystal defects, metallic impurities, polishing faults, scratches, implant inhomogeneities and other effects on wafers with such devices.

The necessary cleanliness for carrying out such measurements is ensured by a flow box and an aerodynamically transparent design.

Figure 1:
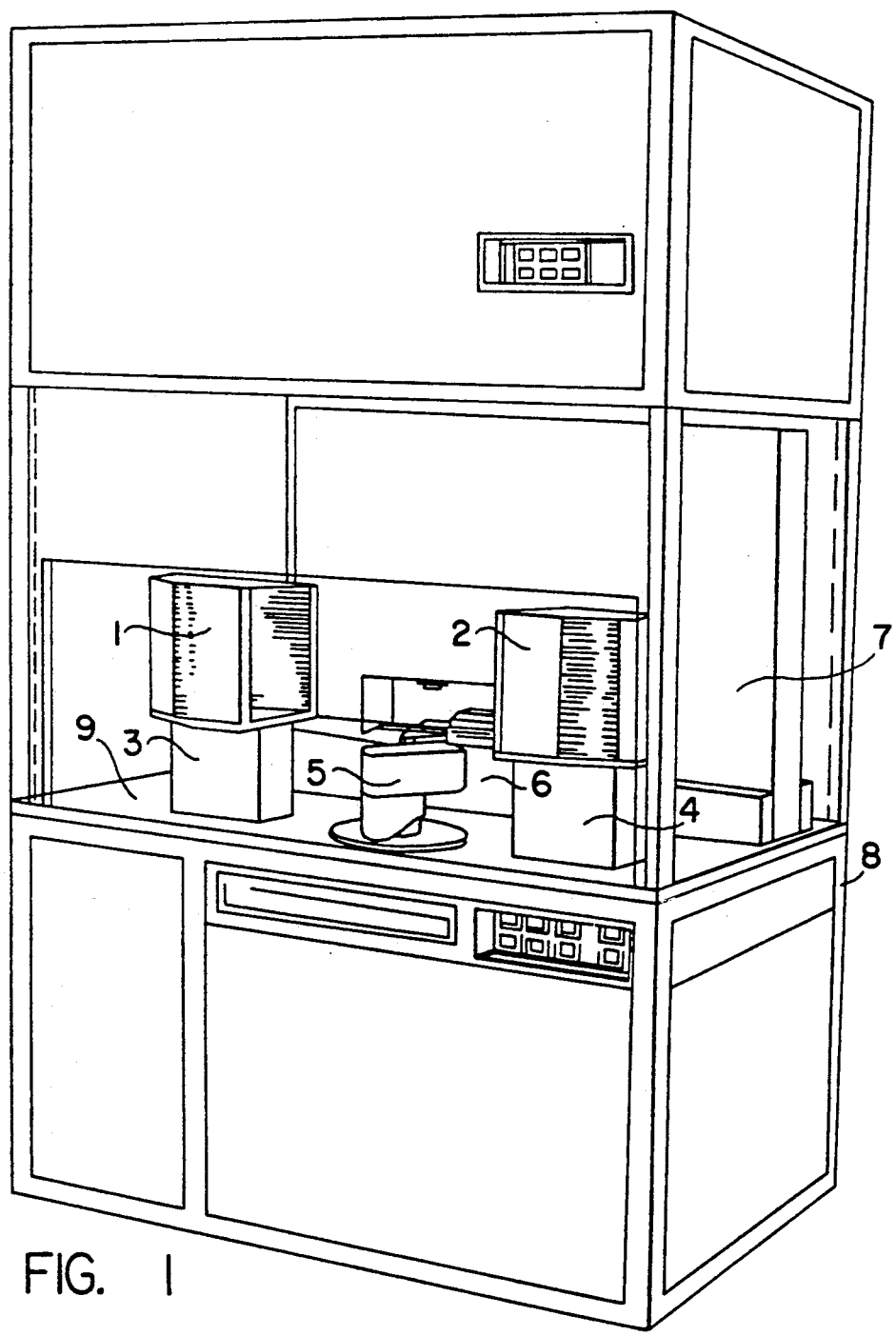
FIG. 1 shows a general illustration of a wafer inspection device in which an arrangement according to the invention is used.
Figure 2:
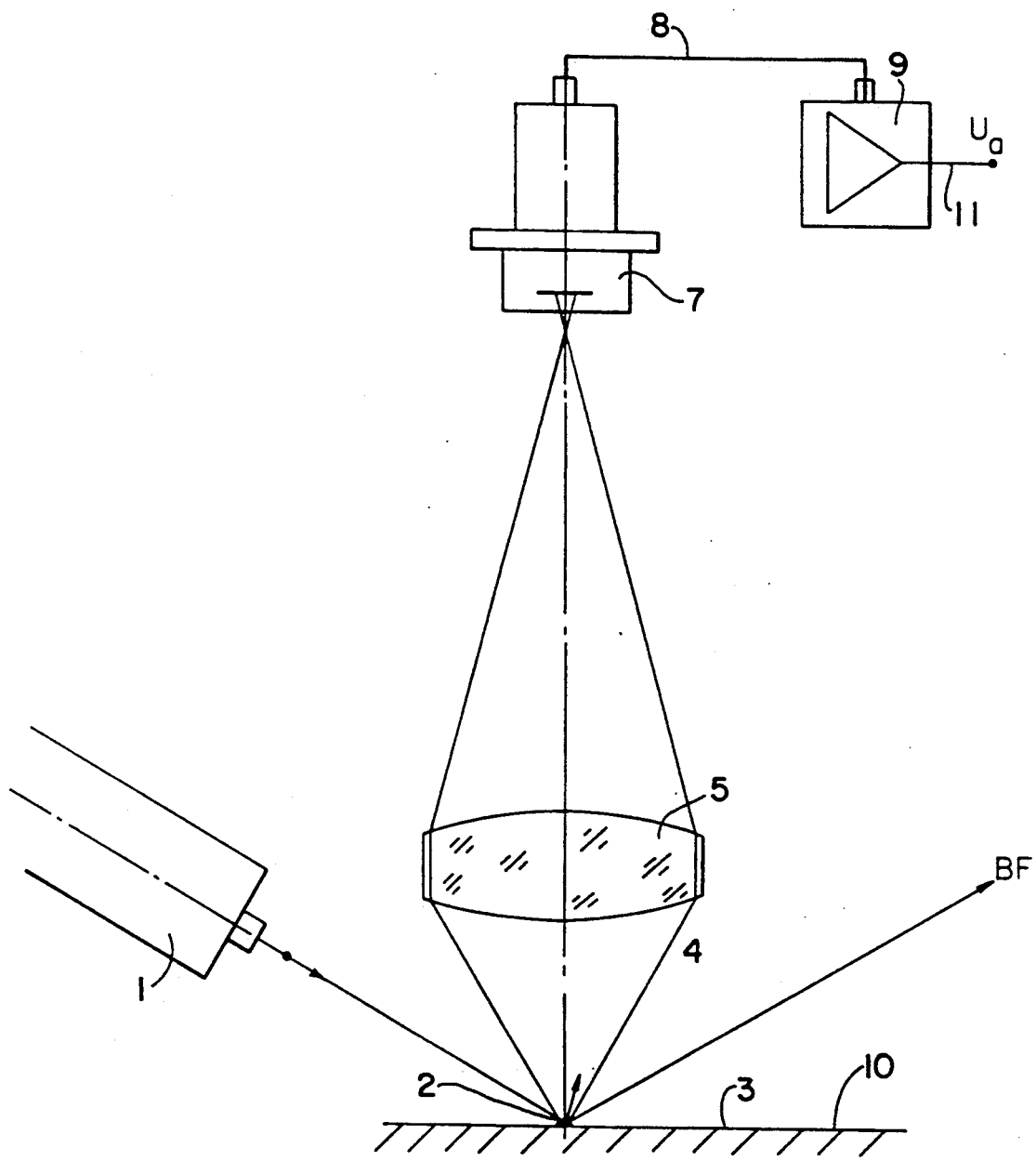
FIG. 2 is a diagrammatic illustration of a known surface inspection scanning device.

FIG. 2 shows a diagrammatic illustration of the state of the art of a surface inspection scanning device which is based on the principle of measuring the elastic scatter. A light source (laser light) 1 illuminates a point 2 on a wafer surface 3. The light reflected from the surface leaves the arrangement in the direction of the arrow BF. A part 4 of the light scattered by the surface is collected by an optical system 5 to be projected into a photodetector 7. An output signal 8 of the photodetector 7 is fed to an amplifier 9. For this procedure the wafer surface 3 lies in the so-called focal plane 10. Now if a defect appears at the illuminated point 2, the proportion of scattered light 4 increases and the intensity E of the light reaching the photodetector 7 increases. The voltage 11 at the output of the amplifier 9 thus likewise increases.

Figure 3:
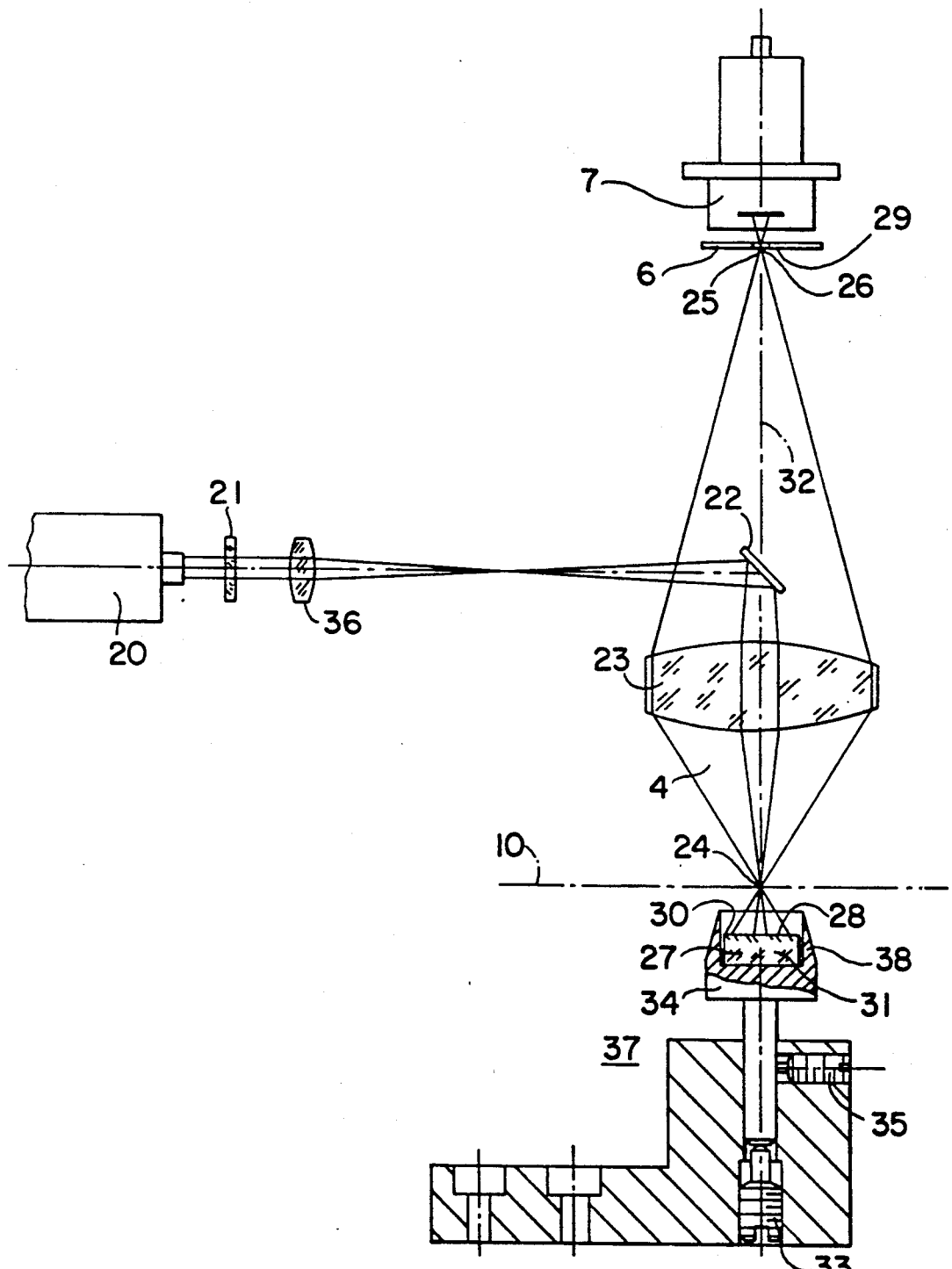
FIG. 3 is a diagrammatic illustration of a first example of an arrangement according to the invention.

FIG. 3 shows a surface inspection scanning device having an arrangement from a surface inspection device for producing defined scattered light amplitudes.

The light emitted from a laser 20 passes through an optical filter 21 (for example a reducer or a neutral-density filter) via a beam deflection means 22 (for example mirror or prism) to a collecting lens 23. The lens focuses the light onto spot 24 lying in the focal plane 10. During the inspection operation, the wafer surface 3 to be inspected lies in the focal plane 10. The part 4 of the scattered light scattered by the wafer surface 3 passes through the collecting lens 23 and the diaphragm 6 to the photodetector 7. The aperture 25 of the diaphragm 6 lies in the image plane 26 of the illuminated spot 24 (confocal system) formed by the collecting lens 23 and has substantially the same shape and dimensions.

During the calibrating phase, a reference medium 27 is preferably disposed below the focal plane 10. Since the reference medium 27 lies outside the focal plane 10, light scattered from it produces a second illuminated spot 28 larger in extent than the first illuminated spot 24 in the focal plane 10.

Likewise in the calibrating phase, the region 29 thus illuminated in the plane of the diaphragm 6 is larger than the image 26.

The aperture 25 of the diaphragm 6 is still the same size, however, so that only a very small proportion of the scattered light passes through the aperture 25 of the diaphragm 6 to the photodetector 7.

Thus a reducing mechanism is formed by means of the optical filter 21 and/or the shift out of the focal plane 10. In addition, the local stability requirement is eliminated by the removal from the focal plane 10 (defocusing) and the associated enlargement of the illuminated spot 24.

Furthermore, a scattering reference medium relying on its volume—a reference medium 27, the scattering capacity of which is not restricted to the surface 30 of the medium but the volume 31 of which constitutes a substantial part of the scattering capacity (milk, milkglass)—on the one hand causes a defocusing in itself and on the other hand prevents the scattering behavior from being able to be varied by external influences.

The size of the illuminated region 29 at the position of the diaphragm 6 can be varied by adjusting the position of the reference medium along the optical axis 32.

Thus with fixed dimensions of the aperture 25 of the diaphragm 6, the amount of energy arriving at the photodetector 7 can be regulated.

In practice, the adjustment operation takes place in accordance with the following procedure. First the intensity E1 of the light illuminating the wafer surface 3 is determined. Then with the reference medium 27 replacing the wafer the intensity E2 of the light reaching the photodetector 7 through the aperture 25 of the diaphragm 6 is measured, the reference medium 27 also being illuminated with an intensity E1. The ratio factor E0 of the two intensities E1 and E2 gives the percentage proportion of that part of the scattered light from the reference medium 27 reaching the photodetector 7.

Now the height of the reference medium 27 can be adjusted so that the required proportion E0 of scattered light from the reference medium always reaches the photodetector.

All surfaces coming up for inspection are then brought into relation with E0.

Thus reproducible and stable values are available for characterizing the surfaces.

FIG. 3 also shows an adjustment mechanism 37 wherein the reference medium 27—consisting of surface 30 and volume 31—is disposed on a support 34 which is adjustable in height by an adjusting screw 33. The support 34 has a rim 38 which prevents unwanted scattered light from being radiated in unintended directions. In this example, the adjustment in height can be fixed by means of a locking screw 35.

Apart from this, it is perfectly possible to integrate at least one diffraction element 36 (for example a lens) between light source 20 and beam deflection means 22.

Figure 4:
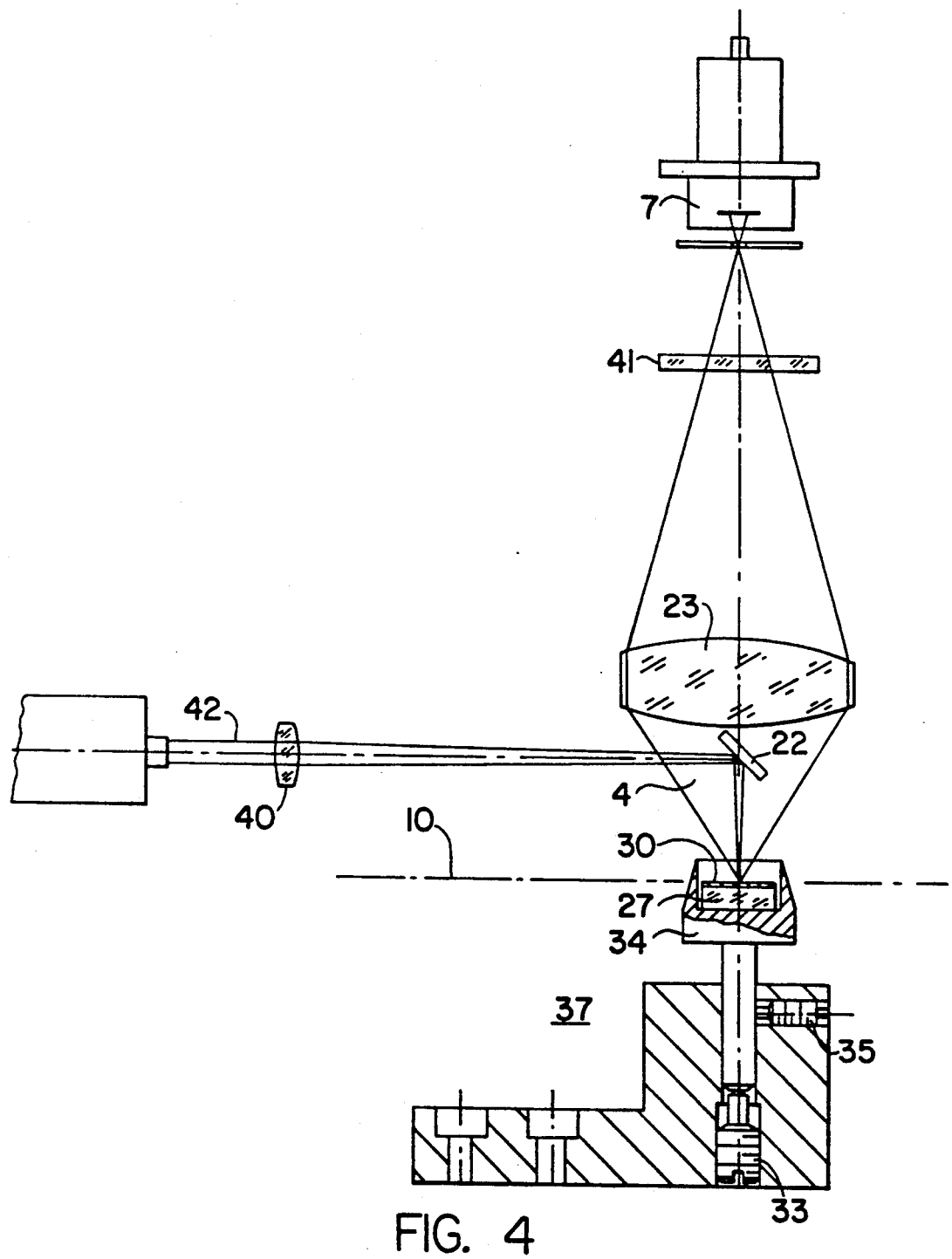
FIG. 4 is a diagrammatic illustration of a second example of an arrangement according to the invention.

Naturally, the lenses, laser sources, diaphragms, optical filters and reference media described here in FIG. 3 and FIG. 4 can be constructed in the form of compound systems and are so in practice. Thus "a lens" for example, generally means a compound lens system, the laser 20 represents in practice a laser source which is composed of two individual sources with different laser light. In the examples described above, however, these details are not gone into for the sake of clarity, and instead special value has been attached to representing the function in detail.

The example in FIG. 4 differs from the arrangement illustrated in FIG. 3 in that the laser light 42 is focused on the wafer surface 3 through a second collecting lens 40, that the surface 30 of the reference medium 27 lies in the focal plane 10, and that an optical reducer 41 is provided in the image-forming part (between beam deflection means 22 and collecting lens 23 or between photosensor 7 and collecting lens 23) of the scattered light 4. In other respects the example in FIG. 4 is precisely the same as that in FIG. 3.

Figure 5A:
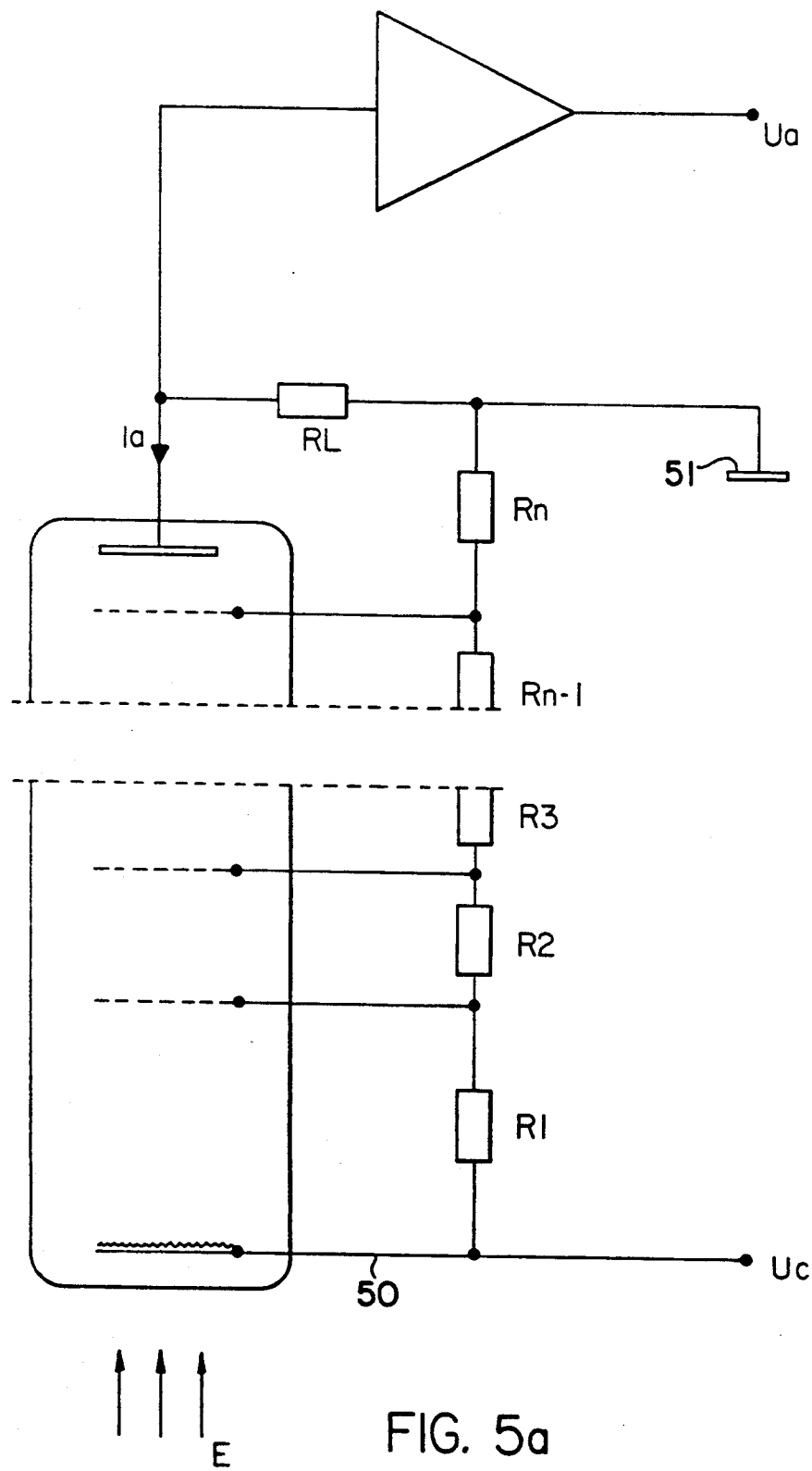
FIG. 5a is a detail circuit diagram for use with the optical systems of both FIG. 3 and FIG. 4.

The part of a circuit described in FIG. 5a comprises a wiring of a photomultiplier of conventional construction with a first connection 50 to which the negative cathode accelerating voltage Uc can be applied. The dynode voltages are taken off via the resistors R1 to Rn which lie between Uc and earth 51. The anode current Ia, which is dependent on the light intensity E and the accelerating voltage Uc, is converted into output voltage Ua by a current-voltage converter.

Figure 5B:
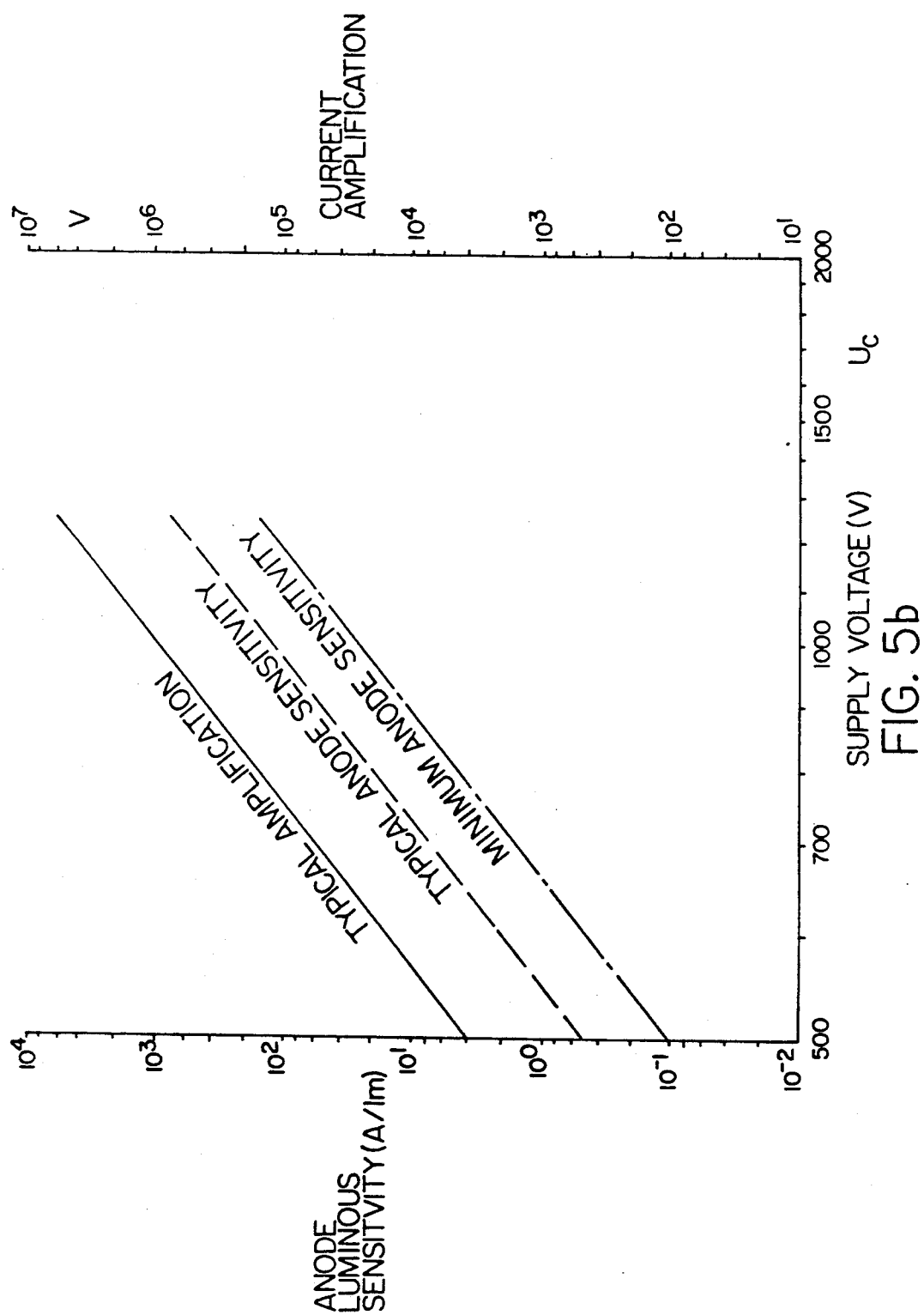
FIG. 5b shows a photomultiplier characteristic curve.

The typical (logarithmic) dependence of the amplification of a photomultiplier on the accelerating voltage Uc is shown in FIG. 5b.

Figure 5C:
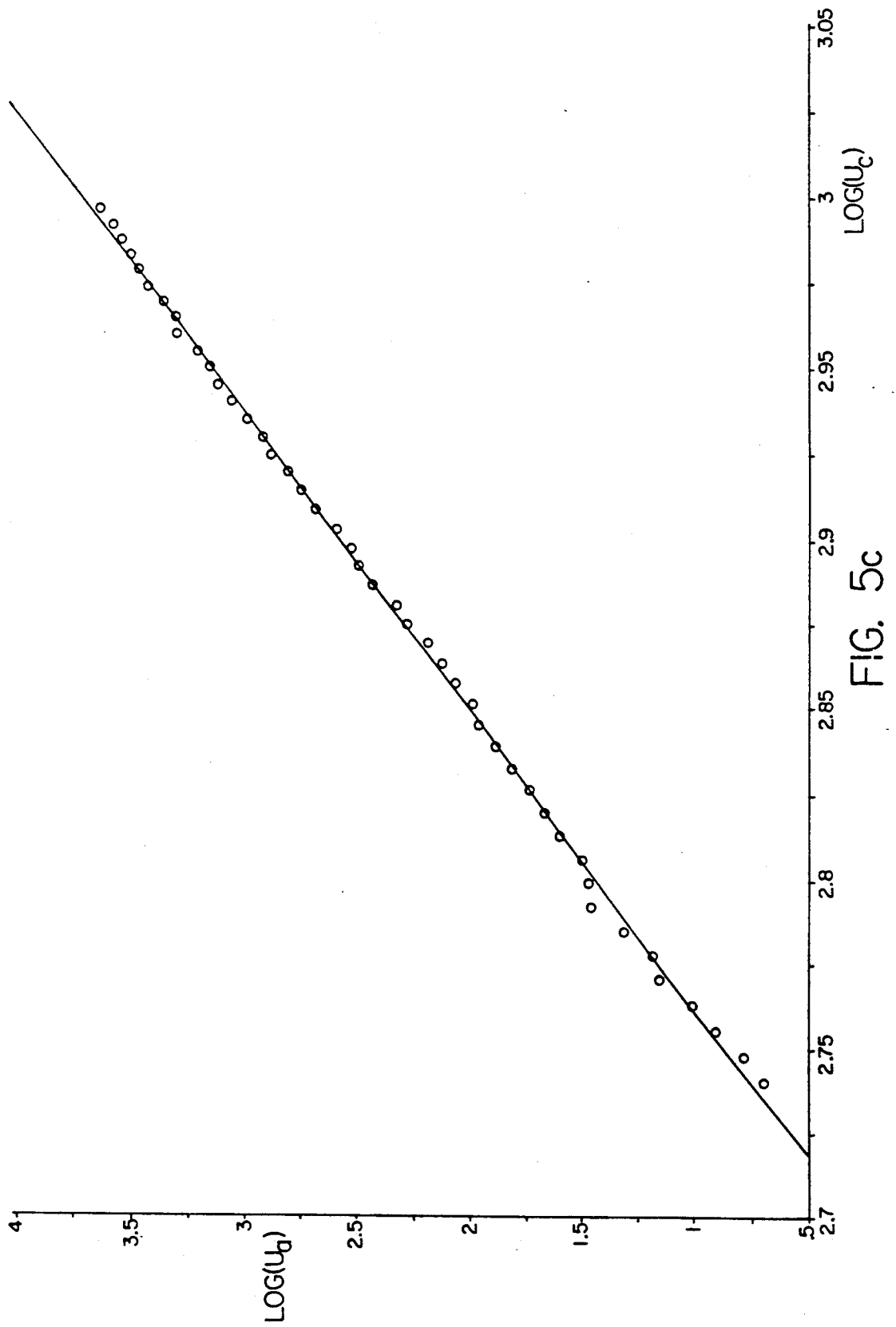
FIG. 5c shows an output characteristic curve with varied photomultiplier accelerating voltage.

The characteristic plotted in FIG. 5c illustrates the relationship between output voltage Ua and accelerating voltage Uc with a constant light intensity E.

The photodetector in the example described is a photomultiplier, the amplification of which is controlled by the accelerating voltage Uc. In order to be able to determine the amplification over the whole accelerating voltage range, additional information is needed, the derivation of which is determined in the manner which can be seen from the flow charts of FIGS. 6a and 6b.

For the calibration, it is important that the photomultiplier should be calibrated as far as possible in the sensitivity range in which it is operated during the measurement. In the present arrangement, therefore, the intensity of light reaching the photomultiplier is reduced by means of an optical filter (reducer).

Figure 6A:
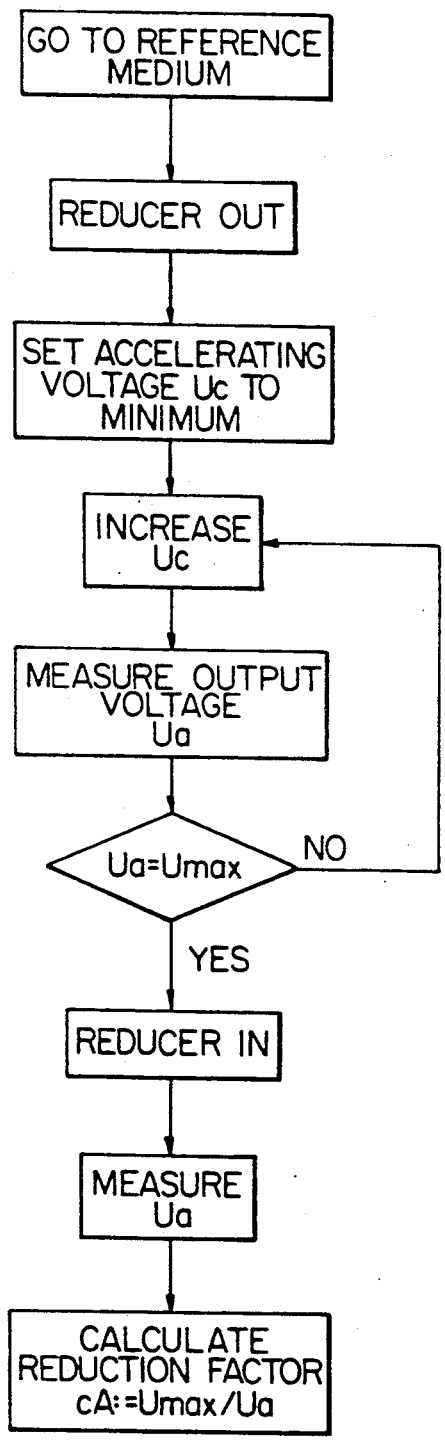
FIG. 6a is a first flow chart of a control sequence of an automatic calibrating operation of the optical filter.

FIG. 6a shows the determination of the reduction factor: first the accelerating voltage is adjusted so that the output voltage Ua is as high as possible without saturating the amplifier 9. The output voltage U1 thus measured is stored, the reducer is brought into the path of rays, and the voltage U2 now appears at the output of the amplifier. The ratio of the two voltages U1 and U2 corresponds to the reduction factor cA of the optical filter.

$$cA = U1/U2 \quad (1)$$

The amplification V of the photomultiplier is $$V = c \cdot Uc\, EXP(a.n) \quad (2)$$

in which n is the known number of dynodes of the photomultiplier and a and c are unknowns depending on the photomultiplier.

Figure 6B:
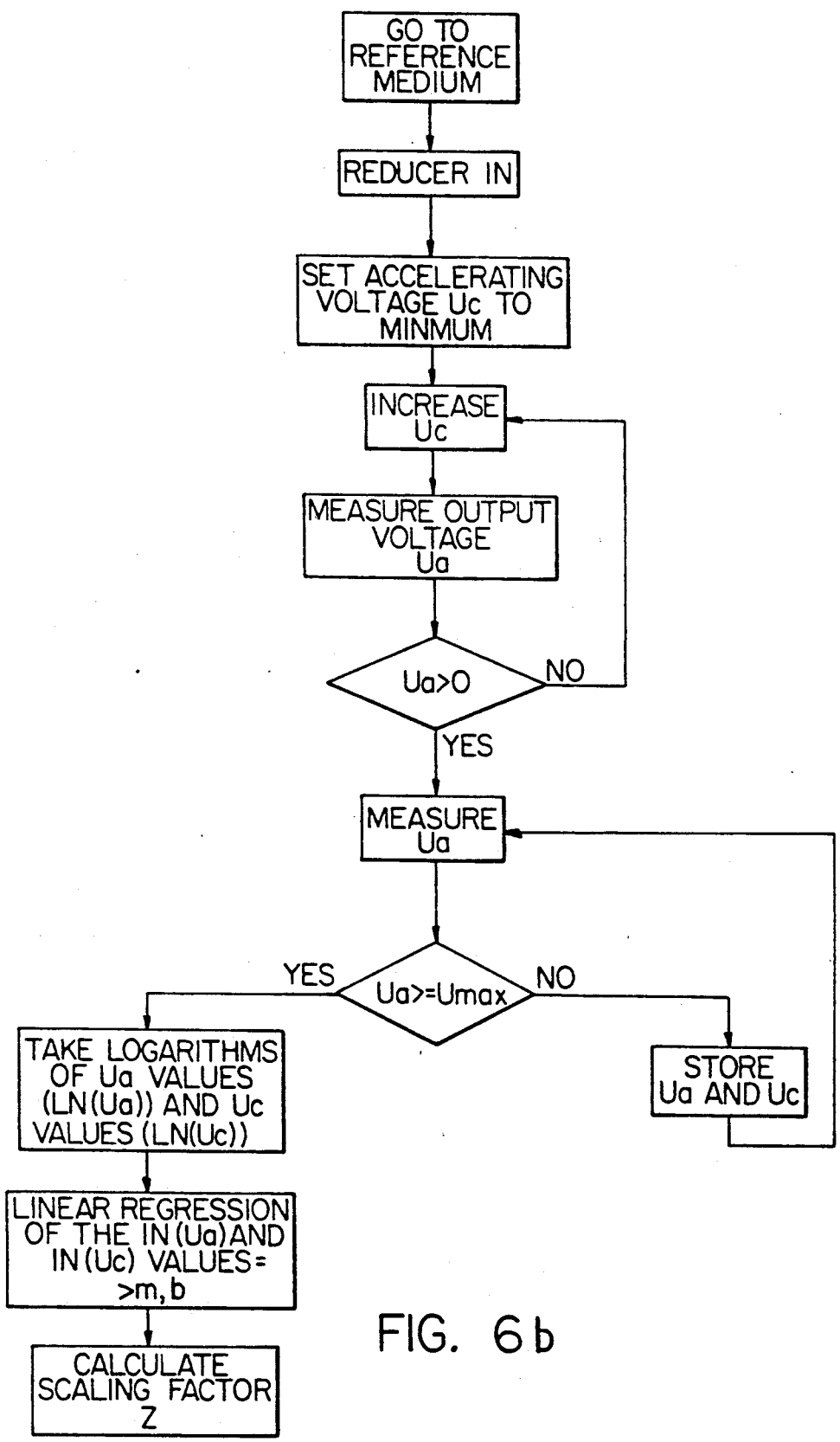
FIG. 6b is a second flow chart of a control sequence of an automatic calibrating operation to determine the conversion factor for the scaling of the measurement results.

In FIG. 6b, the method is used in detail whereby the unknowns are so determined that the amplification V can be calculated for each accelerating voltage Uc.

With the reducer driven into the light path, the output voltage Ua is determined over the whole dynamic range (0 ... Umax) of the amplifier 9. This is realized by step-by-step increase in the accelerating voltage Uc. After each stepped alteration in the accelerating voltage Uc, the output voltage Ua is recorded.

According to (2), the relationship between accelerating voltage Uc and output voltage Ua is $$Ua = c \cdot Uc\, EXP(a.n) \quad (3)$$

By taking the logarithm of (3), the linear relationship $$LOG(Ua) = a \cdot n\, LOG(Uc) + LOG(c) \quad 4)$$

is obtained with a slope m and ordinate portion b, in which $$m = a \cdot n \quad (5)$$

$$b = LOG(c) \quad (6)$$

FIG. 5c shows the graphic illustration of values determined in the above manner. By means of linear regression, m and b can be determined from the measured values.

From the values now determined, a factor z can be formed in order to be able to calculate the scattering component of any wafer surface 3 with an accelerating voltage Uc:

$$z = EO/(cA \cdot EXP(m \cdot LOG(Uc) + b)) \quad (7)$$

The scattered light component Ex of any wafer surface 3 is therefore:

$$Ex = z \cdot Ua \quad (8)$$

Figure 7:
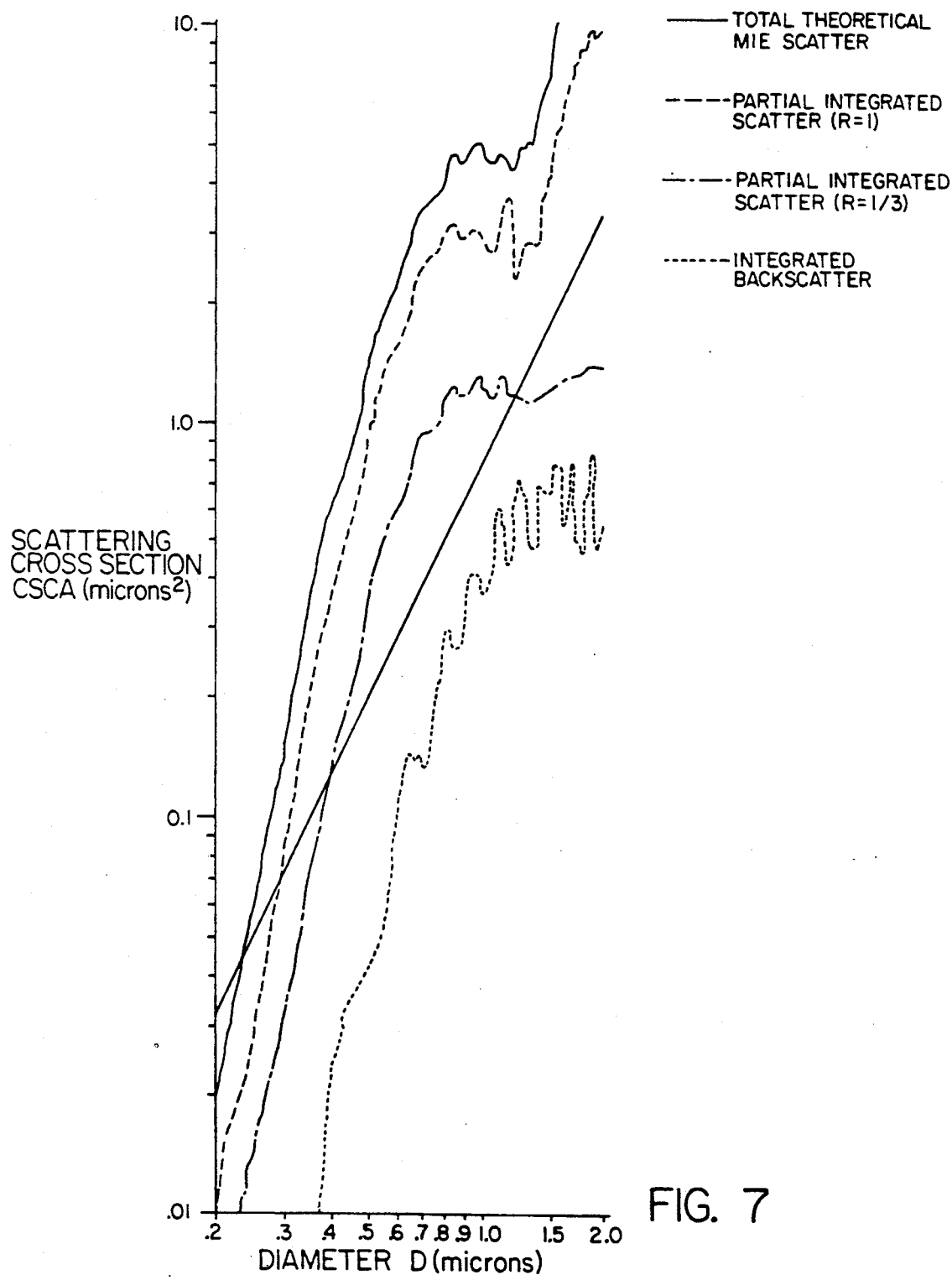
FIG. 7 illustrates the connection between particle size and scattered light intensity.

FIG. 7 shows the connection between particle size (latex balls) and scattered light intensity. This relationship represents the key to determining the size of particles by the scattered light component values given above.

This curve only has to be determined once for each type of machine.

We claim:

1. A method of calibrating a light scanner comprising the steps of
    directing illumination from a light scanner onto a scattering reference medium having a known scattering capacity,
    collecting a portion of the scattered light by means of an optical system having a focal plane,
    defocusing the scattered light collected from the reference medium by disposing the reference medium out of the focal plane of the optical system,
    measuring the amplitude of the scattered light so defocused whereby the local dependence of the scattered light amplitude is eliminated by defocusing the scattered light collected from the reference medium.

2. A method according to claim 1, wherein the reference medium onto which the illumination is directed has a surface of predetermined scattering capacity.

3. A method according to claim 1, wherein the reference medium has a volume effecting the scattering capacity of the medium.

4. A method according to claim 1, wherein a body of milk glass is used as a reference medium.

5. A method according to claim 1 including the additional steps of replacing the reference medium with a substrate having a surface to be inspected, and
    repeating the steps of directing, defocusing and measuring for measuring particles and surface finish on the substrate.

6. An arrangement for producing defined scattered light amplitudes comprising, in combination, a light source for producing a beam of light, an optical filter in the path of said beam, a scattering reference medium with a known scattering capacity, means for directing the beam onto said medium, a photodetector for light from said beam scattered by the reference medium, means including a collecting lens for defocusing light scattered by the reference medium with respect to said photodetector and an amplifier for the output generated by said scattered light on the photodetector.

7. An arrangement according to claim 6, wherein a confocal optical system is employed for directing the scattered light to the photodetector.

8. An arrangement according to claim 6 wherein the means for directing the beam onto the reference medium is focused on a focal plane of the collecting lens and the reference medium is disposed outside the focal plane.

9. An arrangement according to claim 6 wherein the reference medium is a milk glass.

* * * * *